United States Patent [19]
Wertz

[11] Patent Number: 4,817,589
[45] Date of Patent: Apr. 4, 1989

[54] FOOT SUPPORT DEVICE FOR IMPROVED AMBULATION

[76] Inventor: Larry W. Wertz, 3301 Bayshore Blvd., Apt. 2310, Tampa, Fla. 33629

[21] Appl. No.: 89,816

[22] Filed: Aug. 27, 1987

[51] Int. Cl.$^4$ .............................................. A61F 5/00
[52] U.S. Cl. ................................ 128/80 E; 128/80 H
[58] Field of Search .................. 128/80 E, 80 J, 80 H

[56] References Cited

U.S. PATENT DOCUMENTS

| | | | |
|---|---|---|---|
| 2,847,991 | 8/1958 | Andrews | 128/80 E |
| 3,050,053 | 8/1962 | Peckham | 128/80 H |
| 3,073,305 | 1/1963 | Briggs, Jr. et al. | 128/80 H |
| 3,713,437 | 1/1973 | Wiedmer | 128/80 E |
| 3,804,085 | 4/1974 | Eshuis et al. | 128/80 E |
| 3,986,501 | 10/1976 | Schad | 128/80 E |
| 4,329,982 | 5/1982 | Heaney | 128/80 E |
| 4,566,447 | 1/1986 | Deis | 128/80 E |
| 4,597,395 | 7/1986 | Barlow et al. | 128/80 H |
| 4,621,648 | 11/1986 | Ivany | 128/80 H |
| 4,649,939 | 3/1987 | Curtis | 128/80 H |
| 4,729,370 | 3/1988 | Kallassy | 128/80 H |

FOREIGN PATENT DOCUMENTS 280398 12/1930 Italy .................................. 128/80 H

OTHER PUBLICATIONS

Orthopaedic Appliances Atlas, vol. 1, American Academy of Orthopaedic Surgeons, J. W. Edwards, Ann Arbor, Mich., 1952.

*Primary Examiner*—Edgar S. Burr
*Assistant Examiner*—Tonya Lamb
*Attorney, Agent, or Firm*—Kerkam, Stowell, Kondracki & Clarke

[57] ABSTRACT

A comfortable, inconspicuous foot support device is provided to assist a person suffering from foot-drop, the device being adapted to work in combination with a shoe worn by the person, the device having a support member adapted to engage a posterior ankle section of the leg and having strap means for providing dorsiflexion and eversion assistance, the strap means being connected to the support member and attached to predetermined points on the shoe.

22 Claims, 4 Drawing Sheets

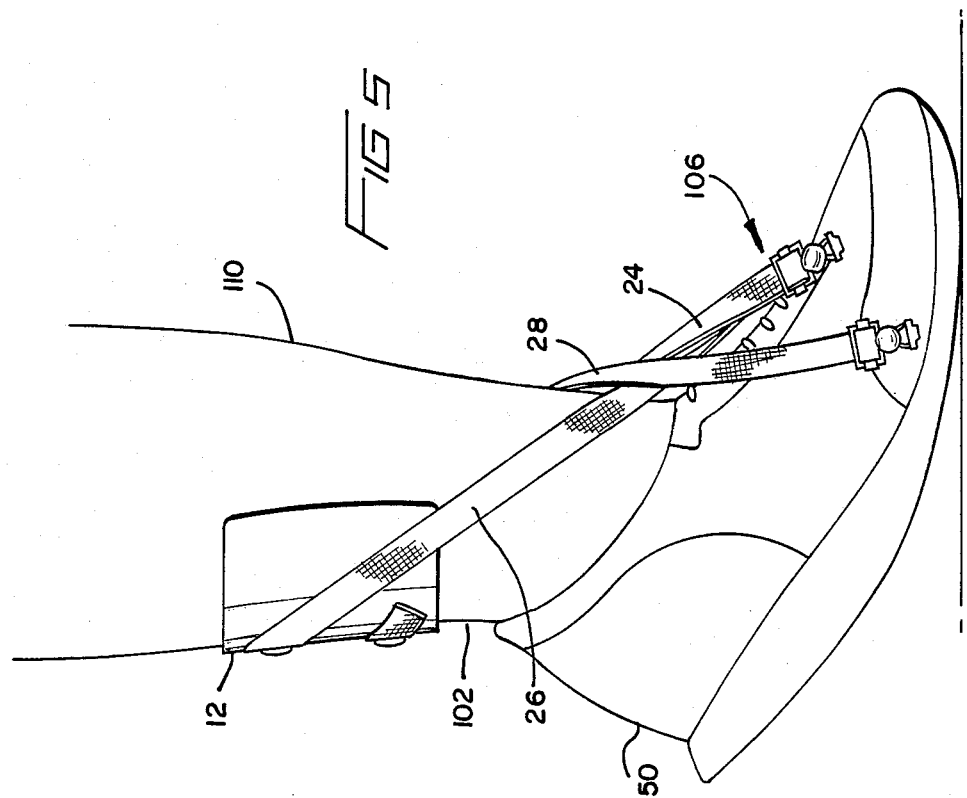
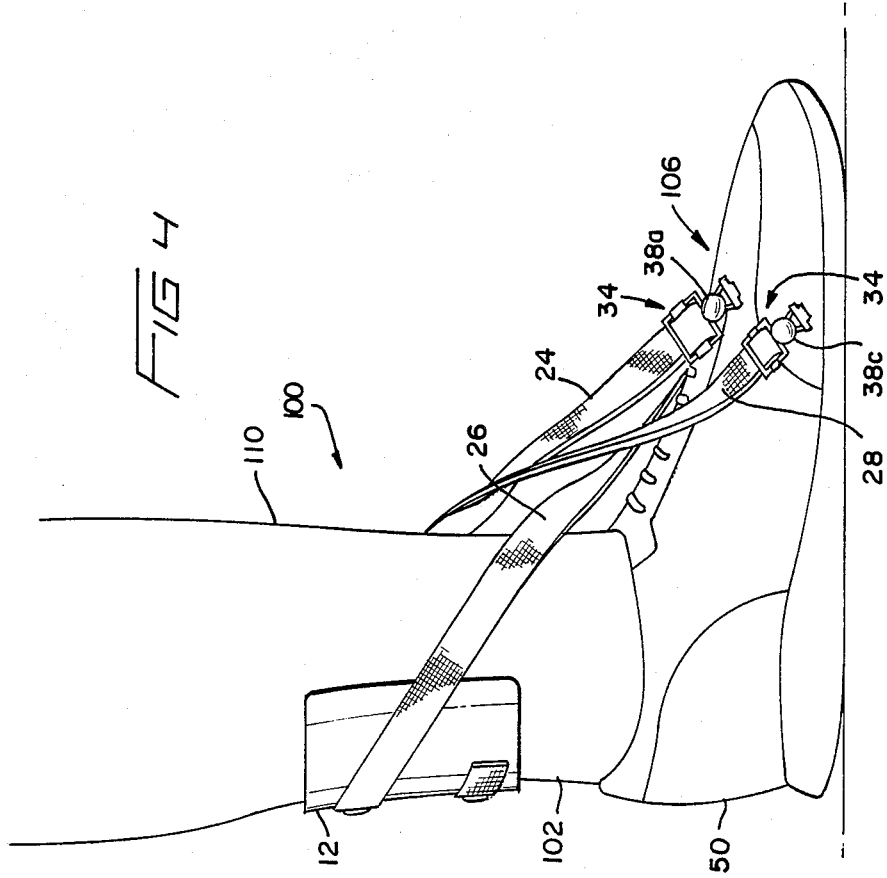

FOOT SUPPORT DEVICE FOR IMPROVED AMBULATION

BACKGROUND OF THE INVENTION

1. Field of the Invention

The present invention relates to an apparatus of the type used to improve the ambulatory or walking motion of persons having foot-drop.

2. Description of Related Art

Foot-drop is characterized in that a person, who otherwise has sufficient muscular control to move his foot relative to his ankle in plantar flexion (a downward push off motion), lacks sufficient muscular control to subsequently effect a dorsiflexion motion to raise the foot back up for the next step. Also usually evidenced in persons having foot-drop is the diminished capacity to move the foot in what is termed eversion, or rotating the outer part of the foot in an upward manner. Where a foot-drop problem is present, walking without the assistance of a brace or support will result in the front (toe) portion of the foot dragging along the ground after the leg and foot have completed the plantar flexion portion of the gait.

Foot-drop is predominately evidenced in stroke victims, although sometimes foot-drop is also evidenced in multiple sclerosis patients, and other orthopedic patients who, for various reasons have suffered a similar loss of muscular control.

A variety of supports have been developed over the years in an effort to assist persons having foot-drop with the hope of enabling them to walk without the foot and toes of the affected leg dragging due to the lack of control over dorsiflexion and eversion motions. Many of these supports accomplish the ultimate goal of raising the toes of the foot, but the disadvantages associated with the use of these support devices detracts from the desire to use such devices. The art has advanced from early known devices which were unsightly, excessively bulky and cumbersome to devices which, although less cumbersome and somewhat more comfortable to wear, still present several shortcomings to the person having to live with the use of a brace or support, not the least of which is external appearance.

Rigid support members have been propounded which are formed in roughly an "L" shape, which conform or substantially conform to the posterior portion of the leg, extending from behind the calf down the leg, behind the heel cord and under the foot. At the top, a band is strapped around the leg, and the bottom portion is secured inside the shoe under the foot. A variant of this type of device is seen in the patent to Schad (U.S. Pat. No. 3,986,501) wherein a rigid member substantially conforming to the posterior portion of the leg extends down the leg from the back of the calf to a cuplike portion at the base of the heel. A strap is provided which extends from the top portion of the rigid member for attachment to the front of the shoe by looping through the shoe's lacing.

These devices provide a brace which is essentially static in nature. The device employing the strap may allow slight movement, but the rigid member will be held tightly against the back of the heel and ankle by the shoe, thereby restricting any substantial movement. Static devices have two primary disadvantages. The first is that, although toe dragging is eliminated, so is all or nearly all of the ability to "push off" while walking, a motion which the foot and leg are capable of performing. This creates an unnatural walking motion commonly associated with the walking motion of a person having a club foot. A second disadvantage is that, in substantially eliminating the ability of the person to "push off" using plantar flexion motion, muscles which the person is capable of using are likely to experience disuse atrophy.

Other more "dynamic" devices have been disclosed in patents to Heaney (U.S. Pat. No. 4,329,982) and Deis (U.S. Pat. No. 4,566,477). These devices provide a band which is wrapped around the leg at or above calf level. Extending from the leg band down to the front of the shoe (or foot) of the wearer is an elastomeric strap member which connects to a loop disposed at or near the toe portion of the shoe. While these devices are likely to provide sufficient force to pull upwardly on the shoe, thus preventing dragging of the toes, the use of a single, long strap does little for the lateral stability of the front of the foot. Additionally, a leg band attached at or above the calf with a strap extending down to the shoe is likely to be conspicuous when worn in public, and may make the wearer more self-conscious of his or her problem. A device of this type is also likely to interfere with the wearing of slacks, as the pant leg will not hang normally, but will have to ride over the elastomeric strap.

The patent to Goffredo (U.S. Pat. No. 2,584,010) shows a band worn just above the ankle. This device shares some of the deficiencies of the other supports described. The use of a strap attached to a point at the front of the brace which is looped through eyelets of the shoe may not contribute sufficiently to the lateral stability of the foot and ankle. Furthermore, this device is not capable of quick attachment and detachment either from the leg or from the shoe, which can result in wearers having to keep the support on at times when they do not actually have a need to wear it. The ankle band must be strapped and unstrapped from the ankle, and the elastic band must be tied and untied from the band and laced and unlaced from the shoe.

It is therefore a principal object of the present invention to provide an improved foot support device for alleviation of foot-drop which will exert sufficient force on a wearer's shoe to raise the front of the foot in dorsiflexion and eversion and also allow the wearer to move his foot in plantar flexion to "push-off" on the foot during ambulation.

It is a further important object of the present invention to provide an improved foot support device which is comfortable to wear both when the user is walking and when stationary.

It is further important object of the present invention to provide a low profile foot support device which is inconspicuous when worn in public.

It is a further important object of the present invention to provide a foot support device which can be easily and quickly attached and detached from the ankle and shoe of the wearer.

SUMMARY OF THE INVENTION

The above and other objects of the present invention are accomplished by a foot support device comprising a low-profile support member which substantially conforms in shape to the portion of the leg behind and above the ankle, and a plurality of elastic strap means attached between the support member and a shoe worn on the person's foot. The elastic strap means which wrap around both sides of the ankle and attach at various predetermined points to a wearer's shoe, provide the required dorsi-flexion and eversion assistance, and improve the lateral stability of the foot, allowing the wearer to walk with a normal or nearly normal gait.

The elastic strap means are connected to the rear portion of the support member at points near both the top and bottom of the support member, which causes the support member to closely follow the motion of the posterior ankle portion of the leg. This allows the foot support device to provide support through the entire range of the walking motion. Having the strap means connected near both the top and bottom also works to distribute the pressure on the posterior ankle portion evenly along the support member, making the device comfortable to wear.

The elastic strap means are provided with attachment means to attach either directly to the shoe or to a complementary attachment means mounted on the shoe. The attachment means preferably is of a quick-disconnect type, allowing the wearer to quickly disengage the straps (and thus the entire device) when it is not needed. The points of attachment will be found at the front side of the ankle at points to either side of the center of the foot, with another attachment point on the outisde part of the foot.

BRIEF DESCRIPTION OF THE DRAWINGS

These and other features of the present and attendant advantages will be readily apparent to those having ordinary skill in the art and the invention will be more easily understood from the following detailed description of the preferred embodiments of the present invention taken in conjunction with the accompanying drawings wherein like reference characters represent like parts throughout the several views.

FIG. 4 is a side view of the foot support device, leg, and shoe in a rest position.

FIG. 5 is a side view of the foot-support device, leg and shoe as they would appear during a "push-off" motion during walking.

DETAILED DESCRIPTION OF THE PREFERRED EMBODIMENT

Figure 1:
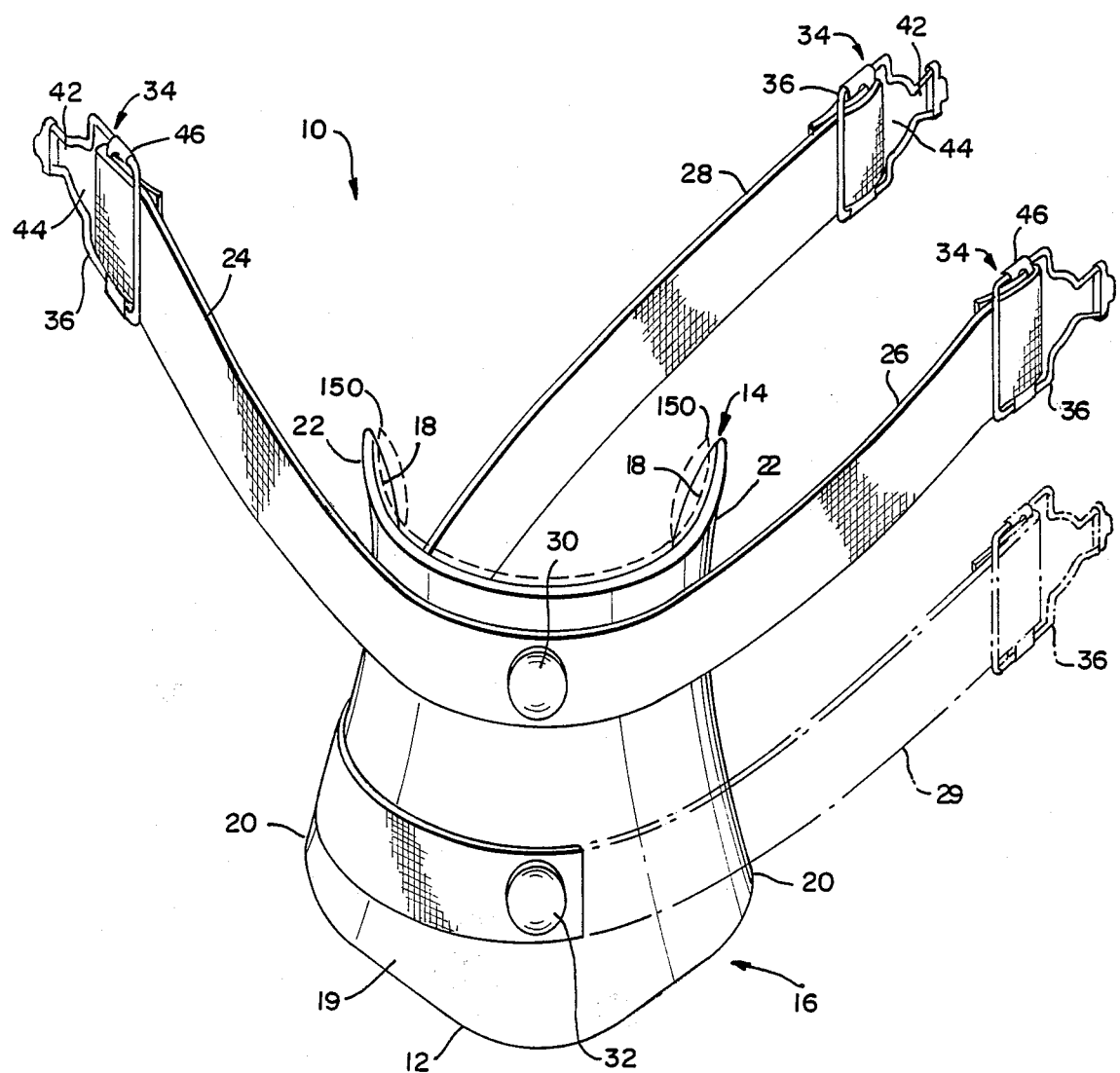
FIG. 1 is a rear perspective view of the foot support device according to the preset invention.

Referring initially to FIG. 1, a foot support device 10 is depicted according to the preferred embodiment of the present invention. Foot support device 10 has a substantially rigid support member 12 which is adapted to engage the posterior ankle section 102 of a wearer's leg 100 (see FIG. 2). As used herein, the term posterior ankle section is intended to encompass an area at the rear of the leg 100, extending vertically from behind the ankle joint and above the heel portion of the foot to a point above the ankle joint below the calf muscles of the leg, and further extending from the most rearward portion of the leg around both sides of the ankle to a point on either side covering approximately half of the protruding ankle bones (the bases of the tibia and fibula).

Support member 12 has a top portion 14 and a bottom portion 16. Because of the importance of providing a foot support device which can be worn comfortably, the interior surface 18 of support member 12 is concave and preferably configured to substantially conform to the shape of the posterior ankle section 102 of the wearer's leg 100. To this end, top portion 14 of the support member 12 is designed to wrap around the rear half of leg 100, but will preferably be flared outwardly at its end 20 relative to the ends 22 of top portion 14. The outward flare accomodates the curvature of the leg near the ankle joint and permits support member 12 to be positioned at a point either immediately above the ankle joint or minimally contacting the top rear part of the ankle joint. As will be explained in more detail in the discussion of FIGS. 4 and 5, this shape and positioning of the support member 12 provides a very comfortable support device both in the rest position and throughout the walking range of motion.

It is recognized that in order for the interior surface 18 of the substantially rigid support member 12 to conform exactly to the shape of a wearer's leg, each support member 12 would have to be custom fitted and manufactured. This is a possibility, and without considering other factors, a custom fitting would be the most preferred way to supply users with the device 10. However, it is also possible, particularly because the support member 12 covers a very small part of the length of the rear of leg 100, to design a support member 12 or a series of support members whose interior surface(s) 18 would substantially conform to the leg shapes of the majority of potential wearers. The primary variation would be in the amount of curvature at the top and bottom portions 14, 16 of the support member 12.

Support member 12 could, for example, be made of a polymeric material which is substantially rigid at normal temperatures (up to 120° F., for example), but which is capable of being deformed after being heated to a higher temperature. The support member 12 would thus be capable of being shaped and formed (to some extent) to more closely fit various sizes and shapes of legs and ankles. The advantage of this type of support member is that it could be stocked as an off-the-shelf item capable of being fitted to most persons, and at the same time would approach the level of conformity of a custom-made support member.

The foot support device 10 provides support to the foot 106 (FIG. 2) of the wearer through a plurality of strap means, preferably made from elastic material each connected at a first end to the support member 12 and at a second end are adapted to be attached to a shoe 50. The strap means thereby provide a means for coupling the support member 12 to a shoe 50 worn on a foot 106 which requires support. In the preferred embodiment, the foot support device 10 has first, second, and third elastic straps 24, 26, and 28 respectively. Generally, first and second elastic straps 24, 26 are used to provide dorsiflexion assistance and lateral foot support. Third elastic strap 28 is used to provide a pulling force to effect eversion of the foot at the same time that first and second straps 24, 26 are pulling foot 106 in a dorsiflexion motion.

As seen in FIG. 1, in the preferred embodiment, the first and second elastic straps 24, 26 are made from the same piece of elastic material. Each of the first, second and third elastic straps 24, 26, 28 have a means for detachably connecting a first end of the strap to support member 12.

As first and second elastic straps share a common first end in this embodiment, the connecting means comprises a single connecting snap 30 adapted to be attached to a complementary snap receiving member (not shown) disposed on the exterior surface 19 of the support member 12, at the top and rear portion thereof. The first end of the third elastic strap 28 also has a connecting snap 32, adapted to be attached to a complementary snap receiving member (not shown) disposed at the bottom and rear portion of support member 12.

Figure 2:
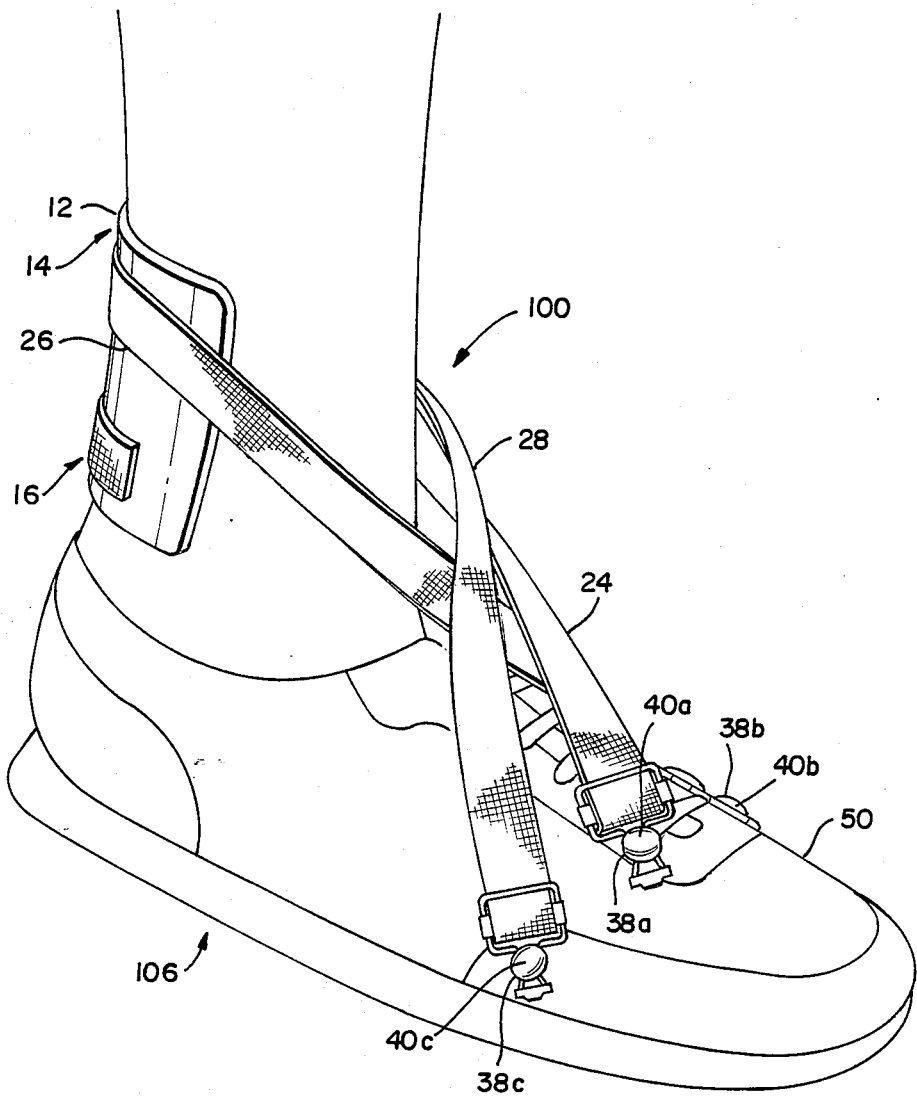
FIG. 2 is a side perspective view of the foot support device of the present invention as viewed from the outer side of a person's leg shown in conjunction with a shoe on the foot of the person.

The elastic straps 24, 26 and 28 should be of sufficient length to be capable of extending from the support member 12 around to the front of a wearer's leg 100 when the support member 12 is placed in position at the back of the ankle. Each of the elastic straps 24, 26, 28 has, at a second end, an attachment means 34 for releaseably attaching the end of the strap to a shoe 50 worn on the foot 106. The attachment means shown on each of the straps in FIG. 1 comprises a wire loop element 36 adapted to engage an associated post 38 mounted on shoe 50 (FIG. 2). The loop 36 and post 38 are of the type well known for use on overalls for connecting the shoulder straps extending over the shoulder from the wearer's back to the bib portion of the overalls (located at the wearer's chest). Posts 38 a, b, and c (FIG. 2) have a short, cylindrical portion extending outwardly from the shoe, the cylindrical portion terminating at a cap or button 40 a, b, c, which has a larger diameter than the cylindrical portion.

The wire loop element 36 has a narrow opening 42 near its tip, the opening 42 being slightly wider than the diameter of the cylindrical portion of post 38. Extending away from the tip, the narrow opening tapers slightly inwardly to a width substantially equal to the diameter of the cylindrical portion of post 38, and then expands to a width slightly greater than the diameter of button 40, and forms an opening of sufficient width and length to permit this wide opening 44 to pass over button 40. The attachment is made by passing button 40 through wide opening 44 and then displacing wire loop element 36 relative to post 38, sliding the narrow opening 42 underneath button 40. An inadvertent disconnection is substantially prevented by the button 40, but an intentional disconnection can be readily and quickly effected. The desirability of this feature is exemplified by a person wearing the support device to work in the morning and being able to easily and quickly remove the device upon reaching his or her desk, where it will not be needed until the person must get up to walk somewhere.

Figure 3:
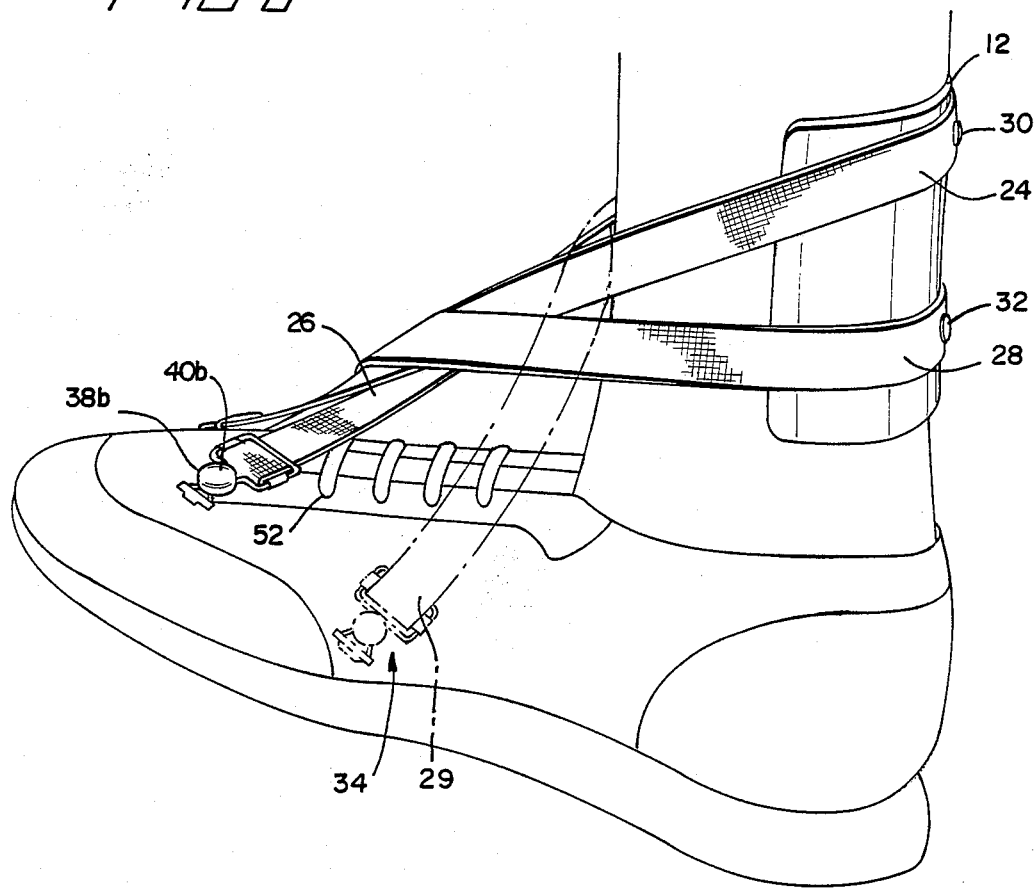
FIG. 3 is a perspective view of the foot support device as it would appear when in use, as viewed from the inner side of a person's leg.

In the preferred embodiment as shown in FIGS. 2 and 3, posts 38 a, b, and c are mounted on the shoe to serve as means for receiving the attachment means of first and second and third elastic straps 24, 26, 28, respectively. Post 38a is disposed on the shoe forward of the ankle joint at what will be termed herein as an outside center part of the foot 106. Post 38b is disposed at approximately the same distance in front of the ankle, but at an inside center part of the foot 106. The spacing between posts 38a and 38b is preferably approximately the width between the pairs of eyelets 52 of the shoe 50, but may be varied, depending on the amount of lateral support required, for example.

Post 38c is disposed on shoe 50 at a point slightly forward of the ankle joint, but near an outer edge of shoe 50 and foot 106. It can be readily appreciated that the location of posts 38 a, b, c, may vary somewhat from shoe to shoe or from wearer to wearer, depending on the particular requirements for support.

It can be seen that first elastic strap 24 will be attached by extending around the inside of leg 100 and crossing over the instep of the foot to be attached at the outside center portion of the foot 50, where post 38a is located. In the same manner, second elastic strap 26 extends from the first end shared with first strap 24 around the outside of leg 100, and crosses over the foot 106 to be attached at the inside center portion of foot 106. Third elastic strap 28 extends from the bottom portion 16 of the support member 12, around the inside of leg 100 and attaches to post 38c near the outer edge of foot 106.

In the figures, third strap 28 is shown as being crossed over the top of first and second straps 24, 26. When attached in this manner, all straps will closely follow the contours of the front of leg 100 and shoe 50. However, the foot support device 10 will work to provide the required support whether third strap 28 extends over or under first and second straps 24, 26.

Posts 38, a, b, c should be mounted to the shoe 50 using means which will not significantly affect the comfort of wearing a shoe. A conventional mounting means used for these posts on bib overalls works well for this application. Mounting is accomplished by having a portion of the post assembly protrude through a small opening in the shoe material to engage a flat-headed member, such that the flat-headed member is disposed in a substantially flush manner with the inside surface of the shoe to minimize any discomfort to the foot. The flat-headed member, having a larger diameter than the opening in the material, prevents post 38 from being pulled away from shoe 50.

Turning now to FIGS. 4 and 5, the operation of the foot support device 10 of the present invention will be described. FIG. 5 shows the leg 100 and foot 106 in a standing or rest position. A person will first put on a sock, if one is to be worn, over the foot 106 and then put on the shoe having the posts 38 a, b, c (FIG. 2) mounted thereon. Support member 12 is then brought into contact at the posterior ankle section 102 of leg 100. The attachment means 34 of each of first, second and third elastic straps 24, 26, 28 are then attached to posts 38a, 38b and 38c, respectively. Thus, only a few seconds more than the time required to put on a sock and shoe are required to also put on the support device 10.

At the rest position, where the foot 106 is roughly at a right angle to the leg 100, the elastic straps 24, 26, 28 should be slightly stretched such that a small pulling force is exerted by each strap at its associated post. This will ensure that the foot will fully return to this position during ambulation and additionally that the support member 12 will be held firmly but not uncomfortably against the back of the leg 100, preventing it from slipping down on the leg.

It is preferred that either the elastic straps or the attachment means disposed at the end of each of the straps have a means for adjusting the length of the strap. As shown in the preferred embodiment of FIG. 5, the wire loop members, 36 are provided with a conventional sliding clamp elements 46 (FIG.) 1 at the point of connection to the straps. Strap length adjustment means are well known in the art, and any suitable means may be used. Providing a foot support device 10 with adjustable length straps allows the tension of the straps to be adjusted to the desired amount. An additional advantage of providing an adjustable length is that the foot support device can be used with a variety of shoe types, each of which may have the posts 38 in slightly different positions, depending on the style of the shoe.

The motion of the leg 100 and foot 106 from the rest position of FIG. 4 during ambulation is shown in FIG. 5. As stated previously, a person having a foot-drop problem will be able to move the foot 106 with respect to the leg 100 in plantar flexion, which is the pushing off motion used in walking and shown in FIG. 5. The plantar flexion motion causes the straps 24, 26, 28 to be further stretched, increasing the tension on the straps between the posts 38 on the shoe 50 and support member 12.

First and second elastic straps 24, 26 are connected to the top portion of support member 12 and third elastic strap 28 is connected to the bottom portion 16, therefore the pressure felt on the posterior ankle section 102 due to the increased tension of the straps is well distributed and will not bring about any sharply focused pressure at a particular point at the back of the leg 100. This arrangement makes the foot support device 10 comfortable to wear throughout the range of walking motion. The support member 12 is prevented from slipping downwardly over the ankle by both the curvature of the ankle joint, and the pressure holding the support member 12 against the back of the leg 100.

While the basic design and arrangement of the support member 12 and straps 24, 26, 28 provides an even distribution of pressure against the back of the leg, further comfort enhancement may be realized by providing a resilient padding on the interior surface 18 of support member 12. The support member 12 may be provided initially with a thin layer of padding 150 (broken lines, FIG. 1) covering the entire interior surface 18. Alternatively, padding may be provided on an "as needed" basis to individual users in the event that part of the leg turns out to be especially sensitive to the pressure of the support member. More localized, possibly thicker padding could be used in this situation, for example, if the user's leg is especially sensitive at the point where the upper end of the support member engages the leg. Several different materials may be used for the padding, foam rubber and loosely woven cotton being two examples.

As the plantar flexion motion is completed, the person's weight is shifted to the other leg and foot as the other foot lands. The foot 106 and leg 100 having the foot support device 10 in place will no longer bear the weight of the body and will be free to be advanced forward of the other foot as is required in normal walking. Without the foot support device, the person could not bring the foot 106 back up into a substantially right angle relation with the leg 100, the toes instead would drag the ground as the foot 106 is advanced. With the foot support device 10 in place, the additional tension created in the straps during the plantar flexion motion acting between support member 12 and posts 38 a, b, c will urge the foot 106 back into an approximately right angle relation with the leg 100.

As indicated previously, a foot-drop problem affects primarily the ability to move the foot 106 in dorsiflexion (upward toward shin 110) and eversion. First and second elastic straps 24, 26 will provide primarily an upward lifting force to assist in dorsiflexion, while third elastic strap 28 supplies a force tending to rotate the outer front portion of the foot 106 in eversion. Improved lateral support for the front of the foot is accomplished with the same elastic straps by having the straps extend around from the sides of the leg to cross over the top of the foot to attachment points on opposite sides.

Figure 6:
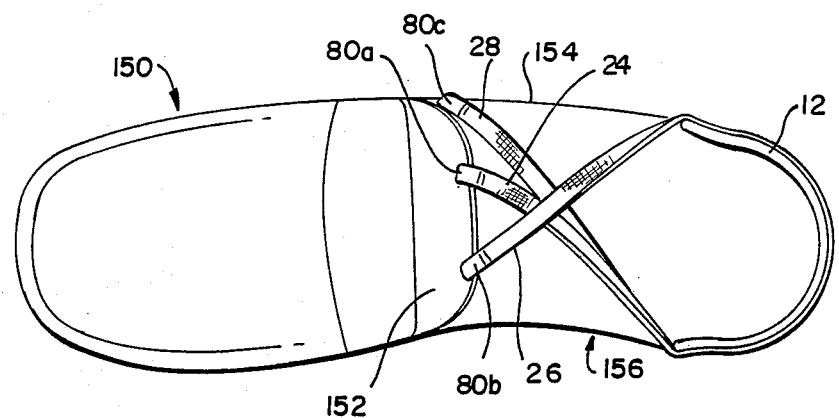
FIG. 6 is a top view of the foot support device of the present invention using an alternative attachment means.

Other embodiments of the foot support device of the present invention are envisioned, one of which is shown in FIG. 6. The foot support device 10 uses the same support member 12 and has three elastic straps 24, 26, 28 which are adapted to be connected between the support member 12 and a shoe 150. In this embodiment, the shoe 150 is a loafer-type shoe. Instead of having wire loop elements as the means for attaching the strap to the shoe, each of straps 24, 26, 28 is provided with a clip 80 a,b,c. These clips operate in a similar manner to clips used to attach suspenders to the waist of a pair of trousers, and actual suspender clips are suitable for use as the attachment means. Because straps 24, 26 and 28 are detachably connected to support member 12, the same support member can be used with both sets of straps depending on what type of shoe is being worn.

It can be seen that the use of clips avoids the need for shoe-mounted posts, or any other complementary fastening means on the shoe. Instead, the receiving means of the shoe are predetermined edge portions of the shoe 150 itself. As in the previously described embodiment, first and second elastic straps extend around the inside and outside (respectively) of the leg 100, and cross over the top portion of the foot. Clips 80a and 80b are attached to tongue 152 at the outside center part and the inside center part, respectively, of shoe 150. Third elastic strap 28 extends around the inside of leg 100 and is attached by clip 80c to a side edge 154 of shoe upper 156. As the straps are in approximately the same positions as in the previously described embodiment, it can readily be envisioned that the straps will operate in much the same manner to effect dorsiflexion and eversion of the foot.

Other variations on the basic foot support device 10 of the present invention are contemplated. In situations where increased lifting forces are deemed to be necessary, a fourth strap means comprising an elastic strap 29 (ghost lines in FIG. 1, FIG. 3) can be used which will extend from a first end detachably connected to the bottom portion of support member 12 around the outside of leg 100, crossing over the top of foot 106 to be removably attached to the inner edge portion of the shoe 50 by attachment means like that used for the other three straps.

Because all of the elastic straps in the preferred embodiment are detachably connected to support member 12, different straps may be used with a single support member for applications demanding different capabilities. The straps may be wider or narrower, or made of different elastic materials in order to provide a foot support device having greater or lesser pulling force for supporting the foot, as required by the particular application.

Additionally, several different means for quickly attaching and detaching the straps from the shoe may be provided as certain shoe styles or personal preferences may demand. In addition to the means previously described and depicted, the straps could be provided with button holes for coupling with either posts 38 or another type of button, or the straps and shoe could employ hooks and eyelets (loops). Other types of quick-attach fasteners can be used provided that they will not inadvertently detach during a walking motion.

Although specific details and elements have been identified in the foregoing description of the preferred embodiments, it is to be appreciated that these are for illustrative purposes only. Numerous modifications and adaptations will be readily apparent to those of ordinary skill in the art. Accordingly, the scope of the present invention should be determined by reference to the appended claims.

What is claimed:

1. A foot support device comprising:
a substantially rigid support member adapted to engage only a posterior portion of a leg of a person at a posterior ankle section of said leg;
a plurality of strap means for assisting said foot in dorsiflexion and eversion movements, said strap means being connected to said support member, said strap means being so constructed and arranged that said strap means are disposed to be releasably attached to a shoe worn on a foot of said person, at least a first one of said strap means extending from an upper portion of said support member around an inside portion of said leg to an outer part of said shoe, at least a second one of said strap means extending from said upper portion of said support member around an outside of said leg to an inner part of said shoe and at least a third one of said strap means extending from a lower portion of said support member around an inside of said leg to a predetermined attachment point at substantially an outer edge of said shoe.

2. A foot support device as defined in claim 1, wherein said strap means are releasably attached to said shoe by attachment means of a quick disconnect type.

3. A combination foot support device and shoe for improving ambulation of a person having foot-drop comprising:
a support member adapted to engage only a back portion of a leg at a position above a heel and below a calf of said leg;
strap means for coupling said support member to said shoe, said strap means further comprising first, second and third straps each having a first end and second end, said first end of each of said first, second, and third straps being connected to said support member, said second end of each strap being provided with means for releasably attaching the straps to said shoe, said shoe having means for receiving said attachment means of said straps, wherein;
said first strap extends from an inside of said leg and is releasably attached to an outside center part of said shoe, said second strap extends from an outside of said leg and is releasably attached to an inside center part of said shoe, and said third strap extends from said inside of said leg and is releasably attached to an outer part of said shoe, and wherein said support member is coupled to said shoe only by said first, second, and third straps.

4. A combination foot support device and shoe as defined in claim 3, wherein at least one of said straps has a means for adjusting the length of the strap.

5. A combination foot support device and shoe as recited in claim 3 wherein said attachment means disposed at the second end of at least one of said first, second and third straps comprises a clip, and wherein said receiving means of said shoe is a edge portion of a predetermined part of said shoe.

6. A combination foot support device and shoe as defined in claim 3, wherein said first, second and third straps are made from an elastically linearly extendable material.

7. A combination foot support device and shoe as defined in claim 6 wherein the means for releasably attaching said straps to said shoe comprises a wire loop element and said receiving means of said shoe comprises posts adapted to receive said wire loop members said posts being mounted to said shoe at predetermined locations.

8. A combination foot support device and shoe as defined in claim 7, wherein said support member is substantially rigid.

9. A combination foot support device and shoe as defined in claim 8 wherein an interior surface of said support member is permanently shaped to substantially conform to a shape of a posterior ankle section of said leg.

10. A combination foot support device and shoe as defined in claim 9 wherein said first and second straps comprise a single elastically linearly extendable strap.

11. A foot support device for improving ambulation of a person having a foot-drop problem, said foot support device being adapted to cooperate with a shoe worn on a foot, comprising:
a support member adapted to engage only a posterior ankle section of a leg, said support member having a top portion and a bottom portion, said bottom portion terminating at a level above said shoe when said foot support device is in position for use; and
a first, second and third strap means for coupling said support member to a shoe worn on said foot, each having a first end connected to said support member and each having a second end, each of said second ends having an attachment means for releasably attaching each of said strap means to said shoe, said support member being coupled to said shoe only by said first, second and third strap means, wherein
said first end of said first strap means is connected to said top portion of said support member and said first strap means extends from said support member at an inside of said leg and is adapted to cross over a top of said foot, whereby said attachment means of said first strap means is disposed to be releasably attached to said shoe at a position in front of said ankle at an outside center part of said foot, and
said first end of said second strap means is connected to said top portion of said support member and said second strap means is adapted to extend from said support member at an outside of said leg and cross over the top of the foot, whereby said attachment means of said second strap means is disposed to be attached to said shoe at a position in front of said ankle at an inside center part of said foot, and
said first end of said third strap means is connected to said bottom portion of said support member and said third strap means extends from said support member at the inside of said leg and is adapted to cross over the top of said foot and extends to a location near an outer part of said foot, whereby said attachment means of said third strap means is disposed to be attached to said shoe at said location near said outer part of said foot.

12. A foot support device as defined in claim 1, further comprising a fourth strap means having a first end connected to said support member and a second end having an attachment means for releasably attaching said fourth strap means to said shoe, said first end of said fourth strap means being connected to said bottom portion of said support member and said fourth strap means extends from said support member at the outside of said leg and crosses over the top of said foot and extends to a location near an inner part of said foot, whereby said attachment means of said fourth strap means is disposed to be attached to said shoe at said location near said inner part of said foot.

13. A foot support device as defined in claim 1, wherein the support member is made from a substantially rigid material.

14. A foot support device as defined in claim 13, wherein an interior surface of said support member is permanently shaped to conform substantially to the shape of the leg at said posterior ankle section.

15. A foot support device as defined in claim 13 wherein said support member has a resilient padding on an interior surface thereof.

16. A foot support device as defined in claim 1, wherein each of said first, second and third strap means includes means for detachably connecting the strap means to said support member.

17. A foot support device as defined in claim 16, wherein each of said first, second and third strap means is an elastic strap, each of said straps being elastically linearly extendable.

18. A foot support device as defined in claim 17, wherein said first and second elastic straps comprise a single piece of elastically linearly extendable material and said piece is detachably connected to said support member by a snap means.

19. A foot support device as defined in claim 17 wherein at least one of said first, second and third elastic straps is adjustable in length.

20. A foot support device as defined in claim 17, wherein each of the attachment means disposed at the second end of at least one of said first, second and third elastic straps comprises a wire loop element.

21. A foot support device as defined in claim 17, wherein at least one of the attachment means disposed at the second end of each of said first, second and third elastic straps comprises a clip.

22. A foot support device as defined in claim 21, wherein the attachment means disposed at each of said second ends of said straps comprises a clip and wherein said clips of said first and second elastic straps are adapted to releasably engage a tongue of said shoe, and said clip disposed at the second end of said third elastic strap is adapted to releasably engage an outer edge of a shoe upper.

* * * * *

UNITED STATES PATENT AND TRADEMARK OFFICE
CERTIFICATE OF CORRECTION

PATENT NO. : 4,817,589
DATED : April 4, 1989
INVENTOR(S) : Larry W. WERTZ

It is certified that error appears in the above-identified patent and that said Letters Patent is hereby corrected as shown below:

Claim 16, line 1, "claim 1" should be --claim 11--

Claim 12, line 1, "claim 1" should be --claim 11--

Claim 13, line 1, "claim 1" should be --claim 11--

Signed and Sealed this

Tenth Day of October, 1989

Attest:

DONALD J. QUIGG

*Attesting Officer*     *Commissioner of Patents and Trademarks*